(12) United States Patent
Kisen et al.

(10) Patent No.: US 7,670,294 B2
(45) Date of Patent: Mar. 2, 2010

(54) NEEDLE GUIDE AND ULTRASONIC BIOPSY PROBE

(75) Inventors: Ryoko Kisen, Tokyo (JP); Osamu Furuta, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1188 days.

(21) Appl. No.: 10/967,393

(22) Filed: Oct. 18, 2004

(65) Prior Publication Data

US 2005/0090741 A1 Apr. 28, 2005

(30) Foreign Application Priority Data

Oct. 24, 2003 (JP) .............................. 2003-364422

(51) Int. Cl.
*A61B 8/00* (2006.01)
(52) U.S. Cl. ...................... 600/459; 600/439; 600/461; 600/462
(58) Field of Classification Search .................. 600/139, 600/459, 461, 437, 439, 443, 454, 462
See application file for complete search history.

(56) References Cited

U.S. PATENT DOCUMENTS

| | | | |
|---|---|---|---|
| 4,058,114 A | 11/1977 | Soldner | |
| 4,349,027 A | 9/1982 | DiFrancesco | |
| 4,469,106 A | 9/1984 | Harui | |
| 4,838,506 A | 6/1989 | Cooper | |
| 4,899,756 A | 2/1990 | Sonek | |
| 5,076,279 A * | 12/1991 | Arenson et al. | 600/461 |
| 5,235,987 A | 8/1993 | Wolfe | |
| 5,427,108 A | 6/1995 | Bollinger | |
| 5,494,039 A | 2/1996 | Onik et al. | |
| 5,623,931 A | 4/1997 | Wung et al. | |
| 5,758,650 A | 6/1998 | Miller et al. | |
| 5,931,787 A * | 8/1999 | Dietz et al. | 600/461 |
| 5,941,889 A | 8/1999 | Cermak | |
| 6,203,499 B1 | 3/2001 | Imling et al. | |
| 6,361,499 B1 | 3/2002 | Bates et al. | |
| 6,368,280 B1 | 4/2002 | Cermak et al. | |
| 6,379,307 B1 | 4/2002 | Filly et al. | |
| 6,475,152 B1 | 11/2002 | Kelly, Jr. et al. | |
| 6,743,177 B2 | 6/2004 | Ito | |
| 7,241,267 B2 * | 7/2007 | Furia | 600/461 |

FOREIGN PATENT DOCUMENTS

| | | |
|---|---|---|
| JP | 7-3607 | 1/1995 |
| JP | 2000-300566 | 10/2000 |

OTHER PUBLICATIONS

A Japanese language Notice of Reasons for Rejection from the Japanese Patent Office.

* cited by examiner

*Primary Examiner*—Brian Casler
*Assistant Examiner*—Baisakhi Roy
(74) *Attorney, Agent, or Firm*—Armstrong Teasdale LLP (57) ABSTRACT

A needle guide includes a straight conduit having a linear passage of an inner diameter that allows passage of the needle and a funnel for increasing the diameter of an opening of the straight conduit at a second end wherein a distance from a center of an opening of the funnel to an ultrasonic probe body is larger than a distance from a center of an opening of the straight conduit at a first end to the ultrasonic probe body.

18 Claims, 6 Drawing Sheets

NEEDLE GUIDE AND ULTRASONIC BIOPSY PROBE

CROSS REFERENCE TO RELATED APPLICATIONS

This application claims the benefit of Japanese Application No. 2003-364422 filed Oct. 24, 2003.

BACKGROUND OF THE INVENTION

The present invention relates to a needle guide and an ultrasonic biopsy probe, and more particularly to a needle guide and an ultrasonic biopsy probe having a structure for preventing a needle from being touched by a hand of an operator.

In the prior art, there is known an ultrasonic biopsy probe comprising an ultrasonic probe body having an elongated trunk provided with ultrasonic transducers at a first end and a cable led out from a second end for conducting ultrasound transmission and reception with the portion in which the ultrasonic transducers are disposed inserted into a subject, and a needle guide having a straight conduit portion into which a needle is inserted, and united with the ultrasonic probe body (e.g., see Patent Documents 1 and 2).

[Patent Document 1]Japanese Patent Application Laid Open No. 2001-299753 (FIGS. 17 and 20).

[Patent Document 2] Japanese Patent Application Laid Open No. H9-238945 (FIG. 2).

In the conventional ultrasonic biopsy probe, an operator positions the needle to align with the center axis of the straight conduit portion in front of an opening of the needle guide, next moves the needle straightforward to insert the needle tip into the opening, and then further moves the needle straightforward.

However, since a hand of the operator holding the ultrasonic probe body lies in front of the opening of the needle guide, there arises a problem that the hand of the operator is likely to touch the needle tip when inserting the needle into the needle guide.

SUMMARY OF THE INVENTION

It is therefore an object of the present invention to provide a needle guide and an ultrasonic biopsy probe having a structure for preventing a needle from being touched by a hand of an operator.

In its first aspect, the present invention provides a needle guide removably united with an ultrasonic probe body, said ultrasonic probe body having an elongated trunk provided with ultrasonic transducers at a first end and a cable led out from a second end for conducting ultrasound transmission and reception with said first end inserted into a subject, said needle guide characterized in comprising a conduit having a first opening and a second opening larger than said first opening, wherein when said needle guide is united with said ultrasonic probe body so that said first opening lies near said first end and said second opening lies near said second end, and a distance between a center of said second opening and said ultrasonic probe body is larger than a distance between a center of said first opening and said ultrasonic probe body.

The term the "center of an opening" refers to a midpoint of the shortest line connecting on the opening face a point on a periphery of the opening that is closest to the ultrasonic probe body and a point on the periphery of the opening that is farthest from the ultrasonic probe body when the needle guide is united with the ultrasonic probe body.

In the needle guide of the first aspect, the area of the second opening through which the needle is inserted is enlarged and the distance from the ultrasonic probe body to the center of the second opening is increased. Thus, when the operator conducts an operation involving positioning the needle tip near the center of the second opening in front of the second opening, next moving the needle toward the second opening to insert the needle tip into the second opening, and then moving the needle toward the center of the first opening, since the distance from the ultrasonic probe body to the center of the second opening is increased relative to the conventional case, the distance between the needle tip when the needle is inserted into the needle guide and the hand of the operator holding the ultrasonic probe body is increased. Moreover, since the needle can be obliquely held to insert the needle tip into the second opening, it is easier to control the needle tip than in an operation of inserting the needle tip into the second opening while horizontally holding the needle. Thus, the needle tip is prevented from being touched by the hand of the operator.

In its second aspect, the present invention provides the needle guide having the aforementioned configuration, characterized in that: an opening face of said second opening is oblique with respect to the center axis of said elongated trunk when said needle guide is united with said ultrasonic probe body.

The "opening face" may be planar or curved. The term "oblique" and the like refers to a condition in which a straight line connecting a point on a periphery of the opening that is closest to the ultrasonic probe body and a point on the periphery of the opening that is farthest from the ultrasonic probe body when the needle guide is united with the ultrasonic probe body forms an angle other than 90° with respect to the center axis of the elongated trunk.

When inserting a needle into a face, in many cases, one tries to insert the needle tip as perpendicularly to the face as possible.

Accordingly, in the needle guide of the second aspect, the opening face of the second opening is made oblique with respect to the center axis of the elongated trunk of the ultrasonic probe body. As a result, the operator tries to insert the needle tip into the opening face of the second opening while holding the needle obliquely with respect to the elongated trunk of the ultrasonic probe body. Since the needle tip thus comes closest to the hand of the operator holding the ultrasonic probe body, if the operator focuses his/her attention to the needle tip to insert the needle into the second opening, no portion of the needle is touched by the hand of the operator holding the ultrasonic probe body. Moreover, since the needle tip can be inserted into the second opening while obliquely holding the needle, it is easier to control the needle tip than in an operation of inserting the needle tip into the second opening while horizontally holding the needle.

In its third aspect, the present invention provides the needle guide having the aforementioned configuration, characterized in that: the opening face of said second opening is a bent face created by connecting two planes at different angles with respect to the center axis of said elongated trunk when said needle guide is united with said ultrasonic body.

The "two planes" may be both flat, both curved, or one may be flat and the other curved.

In the needle guide of the third aspect, since there are two planes, one at an angle relatively near 0° and the other at an angle relatively near 90° with respect to the center axis of the elongated trunk of the ultrasonic probe body, the operator can move the needle with reference to one surface when inserting the needle tip into the second opening, and with reference to the other plane when moving the needle toward the center of the first opening, thereby facilitating operation.

In its fourth aspect, the present invention provides the needle guide having the aforementioned configuration, characterized in that: said needle guide comprises a straight conduit portion having a linear passage of an inner diameter that allows passage of the needle, and a funnel portion formed by increasing the diameter of an opening of said straight conduit portion at one end, wherein said needle guide is united with said ultrasonic probe body so that said straight conduit portion lies near said first end and said funnel portion lies near said second end, a center of an opening of said funnel portion is offset from the center axis of said straight conduit portion so that a distance between the center of the opening of said funnel portion and said ultrasonic probe body is larger than a distance between a center of an opening of said straight conduit portion at the other end and said ultrasonic probe body.

In the needle guide of the fourth aspect, the area of the opening through which the needle is inserted is enlarged using the funnel portion, and the distance from the ultrasonic probe body to the center of the opening of the funnel portion is increased. Thus, when the operator conducts an operation involving positioning the needle tip near the center of the opening of the funnel portion in front of the opening of the funnel portion, next moving the needle toward the opening of the funnel portion to insert the needle tip into the opening of the funnel portion, and then moving the needle toward the straight conduit portion, since the distance from the ultrasonic probe body to the center of the opening of the funnel portion is increased relative to the conventional case, the distance between the needle tip when the needle is inserted into the needle guide and the hand of the operator holding the ultrasonic probe body is increased. Moreover, since the needle can be obliquely held to insert the needle tip into the opening of the funnel portion, it is easier to control the needle tip than in an operation of inserting the needle tip into the opening of the funnel portion while horizontally holding the needle. Thus, the needle tip is prevented from being touched by the hand of the operator.

In its fifth aspect, the present invention provides the needle guide having the aforementioned configuration, characterized in that: an opening face of said funnel portion is oblique with respect to the center axis of said straight conduit portion.

When inserting a needle into a face, in many cases, one tries to insert the needle tip as perpendicularly to the face as possible.

Accordingly, in the needle guide of the fifth aspect, the opening face of the funnel portion is made oblique with respect to the center axis of the elongated trunk of the ultrasonic probe body. As a result, the operator tries to insert the needle tip into the opening face of the funnel portion while holding the needle obliquely with respect to the elongated trunk of the ultrasonic probe body. Since the needle tip thus comes closest to the hand of the operator holding the ultrasonic probe body, if the operator focuses his/her attention to the needle tip to insert the needle into the funnel portion, no portion of the needle is touched by the hand of the operator holding the ultrasonic probe body. Moreover, since the needle tip can be inserted into the opening of the funnel portion while obliquely holding the needle, it is easier to control the needle tip than in an operation of inserting the needle tip into the opening of the funnel portion while horizontally holding the needle.

In its sixth aspect, the present invention provides the needle guide having the aforementioned configuration, characterized in that: the opening face of said funnel portion is a bent face created by connecting two planes at different angles with respect to the center axis of said straight conduit portion.

In the needle guide of the sixth aspect, since there are two planes, one at an angle relatively near 0° and the other at an angle relatively near 90° with respect to the center axis of the elongated trunk of the ultrasonic probe body, the operator can move the needle with reference to one surface when inserting the needle tip into the opening of the funnel portion, and with reference to the other plane when moving the needle toward the center of the straight conduit portion, thereby facilitating operation.

In its seventh aspect, the present invention provides the needle guide having the aforementioned configuration, characterized in that: said needle guide comprises a flared tube having a passage outspreading from a first opening to a second opening larger than said first opening, wherein said needle guide is united with said ultrasonic probe body so that said first opening lies near said first end and said second opening lies near said second end, and a distance between a center of said second opening and said ultrasonic probe body is larger than a distance between a center of said first opening and said ultrasonic probe body.

In the needle guide of the seventh aspect, the area of the second opening through which the needle is inserted is enlarged, and the distance from the ultrasonic probe body to the center of the second opening is increased. Thus, when the operator conducts an operation involving positioning the needle tip near the center of the second opening in front of the second opening, next moving the needle toward the second opening to insert the needle tip into the second opening, and then moving the needle toward the center of the first opening, since the distance from the ultrasonic probe body to the center of the second opening is increased relative to the conventional case, the distance between the needle tip when the needle is inserted into the needle guide and the hand of the operator holding the ultrasonic probe body is increased. Moreover, since the needle can be obliquely held to insert the needle tip into the second opening, it is easier to control the needle tip than in an operation of inserting the needle tip into the second opening while horizontally holding the needle. Thus, the needle tip is prevented from being touched by the hand of the operator.

In its eighth aspect, the present invention provides the needle guide having the aforementioned configuration, characterized in that: when a needle is abutted against a first opening top portion and a second opening bottom portion, said needle is oblique with respect to the center axis of said elongated trunk.

In this configuration, the "first opening top portion" refers to a point on a periphery of the first opening that is farthest from the ultrasonic probe body and the vicinity of the point. The "second opening bottom portion" refers to a point on a periphery of the second opening that is closest to the ultrasonic probe body and the vicinity of the point.

In the needle guide of the eighth aspect, since a needle-pricking operation can be done while obliquely holding the needle, it is easier to control the needle tip than in an operation with the horizontally held needle.

In its ninth aspect, the present invention provides the needle guide having the aforementioned configuration, characterized in that: said needle guide comprises a straight conduit portion having a linear passage of an inner diameter that allows passage of the needle, a funnel portion formed by increasing the diameter of an opening of said straight conduit portion at one end, and a fastener for uniting said needle guide with said ultrasonic probe body so that said straight conduit portion lies near said first end and said funnel portion lies near said second end, wherein when said needle guide is united with said ultrasonic body, said fastener achieves the uniting while making the center axis of said straight conduit portion oblique with respect to the center axis of said elongated trunk so that a distance between a center of the opening of said funnel portion and said ultrasonic probe body is larger than a distance between a center of the opening of said straight conduit portion at the other end and said ultrasonic probe body.

In the needle guide of the ninth aspect, the area of the opening through which the needle is inserted is enlarged using the funnel portion, and the distance from the ultrasonic probe body to the center of the opening of the funnel portion is increased. Thus, when the operator conducts an operation involving positioning the needle tip near the center of the opening of the funnel portion in front of the opening of the funnel portion, next moving the needle toward the opening of the funnel portion to insert the needle tip into the opening of the funnel portion, and then moving the needle toward the straight conduit portion, since the distance from the ultrasonic probe body to the center of the opening of the funnel portion is increased relative to the conventional case, the distance between the needle tip when the needle is inserted into the needle guide and the hand of the operator holding the ultrasonic probe body is increased. Moreover, since the needle can be obliquely held to insert the needle tip into the opening of the funnel portion, it is easier to control the needle tip than in an operation of inserting the needle tip into the opening of the funnel portion while horizontally holding the needle. Thus, the needle tip is prevented from being touched by the hand of the operator.

In its tenth aspect, the present invention provides an ultrasonic biopsy probe comprising an ultrasonic probe body and a needle guide united with said ultrasonic probe body, said ultrasonic probe body having an elongated trunk provided with ultrasonic transducers at a first end and a cable led out from a second end for conducting ultrasound transmission and reception with said first end inserted into a subject, said ultrasonic biopsy probe characterized in that: said needle guide comprises a conduit having a first opening and a second opening larger than said first opening, wherein when said needle guide is united with said ultrasonic probe body so that said first opening lies near said first end and said second opening lies near said second end, and a distance between a center of said second opening and said ultrasonic probe body is larger than a distance between a center of said first opening and said ultrasonic probe body.

The needle guide may be united with the ultrasonic probe body by being removably attached thereto or by being incorporated in the ultrasonic probe body.

In the ultrasonic biopsy probe of the tenth aspect, the needle tip is prevented from being touched by the hand of the operator by the same effect as in the needle guide of the first aspect.

In its eleventh aspect, the present invention provides the ultrasonic biopsy probe having the aforementioned configuration, characterized in that: an opening face of said second opening is oblique with respect to the center axis of said elongated trunk when said needle guide is united with said ultrasonic probe body.

In the ultrasonic biopsy probe of the eleventh aspect, the needle tip is prevented from being touched by the hand of the operator by the same effect as in the needle guide of the second aspect.

In its twelfth aspect, the present invention provides the ultrasonic biopsy probe having the aforementioned configuration, characterized in that: the opening face of said second opening is a bent face created by connecting two planes at different angles with respect to the center axis of said elongated trunk when said needle guide is united with said ultrasonic body.

In the ultrasonic biopsy probe of the twelfth aspect, the needle tip is prevented from being touched by the hand of the operator by the same effect as in the needle guide of the third aspect.

In its thirteenth aspect, the present invention provides the ultrasonic biopsy probe having the aforementioned configuration, characterized in that: said needle guide comprises a straight conduit portion having a linear passage of an inner diameter that allows passage of the needle, and a funnel portion formed by increasing the diameter of an opening of said straight conduit portion at one end, wherein said needle guide is united with said ultrasonic probe body so that said straight conduit portion lies near said first end and said funnel portion lies near said second end, a center of an opening of said funnel portion is offset from the center axis of said straight conduit portion so that a distance between the center of the opening of said funnel portion and said ultrasonic probe body is larger than a distance between a center of an opening of said straight conduit portion at the other end and said ultrasonic probe body.

In the ultrasonic biopsy probe of the thirteenth aspect, the needle tip is prevented from being touched by the hand of the operator by the same effect as in the needle guide of the fourth aspect.

In its fourteenth aspect, the present invention provides the ultrasonic biopsy probe having the aforementioned configuration, characterized in that: an opening face of said funnel portion is oblique with respect to the center axis of said straight conduit portion.

In the ultrasonic biopsy probe of the fourteenth aspect, the needle tip is prevented from being touched by the hand of the operator by the same effect as in the needle guide of the fifth aspect.

In its fifteenth aspect, the present invention provides the ultrasonic biopsy probe having the aforementioned configuration, characterized in that: the opening face of said funnel portion is a bent face created by connecting two planes at different angles with respect to the center axis of said straight conduit portion.

In the ultrasonic biopsy probe of the fifteenth aspect, the needle tip is prevented from being touched by the hand of the operator by the same effect as in the needle guide of the sixth aspect.

In its sixteenth aspect, the present invention provides the ultrasonic biopsy probe having the aforementioned configuration, characterized in that: said needle guide comprises a flared tube having a passage outspreading from a first opening to a second opening larger than said first opening, wherein said needle guide is united with said ultrasonic probe body so that said first opening lies near said first end and said second opening lies near said second end, and a distance between a center of said second opening and said ultrasonic probe body is larger than a distance between a center of said first opening and said ultrasonic probe body.

In the ultrasonic biopsy probe of the sixteenth aspect, the needle tip is prevented from being touched by the hand of the operator by the same effect as in the needle guide of the seventh aspect.

In its seventeenth aspect, the present invention provides the ultrasonic biopsy probe having the aforementioned configuration, characterized in that: when a needle is abutted against a first opening top portion and a second opening bottom portion, said needle is oblique with respect to the center axis of said elongated trunk.

In the ultrasonic biopsy probe of the seventeenth aspect, the needle tip is prevented from being touched by the hand of the operator by the same effect as in the needle guide of the eighth aspect.

In its eighteenth aspect, the present invention provides the ultrasonic biopsy probe having the aforementioned configuration, characterized in that: said needle guide comprises a straight conduit portion having a linear passage of an inner diameter that allows passage of the needle, a funnel portion formed by increasing the diameter of an opening of said straight conduit portion at one end, and a fastener for uniting said needle guide with said ultrasonic probe body so that said straight conduit portion lies near said first end and said funnel portion lies near said second end, wherein when said needle guide is united with said ultrasonic body, said fastener achieves the uniting while making the center axis of said straight conduit portion oblique with respect to the center axis of said elongated trunk so that a distance between a center of the opening of said funnel portion and said ultrasonic probe body is larger than a distance between a center of the opening of said straight conduit portion at the other end and said ultrasonic probe body.

In the ultrasonic biopsy probe of the eighteenth aspect, the needle tip is prevented from being touched by the hand of the operator by the same effect as in the needle guide of the ninth aspect.

According to the needle guide and ultrasonic biopsy probe of the present invention, since the distance between the needle tip when the needle is inserted into the needle guide and the hand of the operator holding the ultrasonic probe body is increased and the needle can be obliquely held to insert the needle tip into the opening, it is easier to control the needle tip. Thus, the needle tip is prevented from being touched by the hand of the operator.

The needle guide and ultrasonic biopsy probe of the present invention may be employed as a needle guide and an ultrasonic biopsy probe to be inserted into the vagina to conduct needle prick.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to embodiments shown in the accompanying drawings. It should be noted that the present invention is not limited to these embodiments.

EXAMPLE 1

Figure 1:
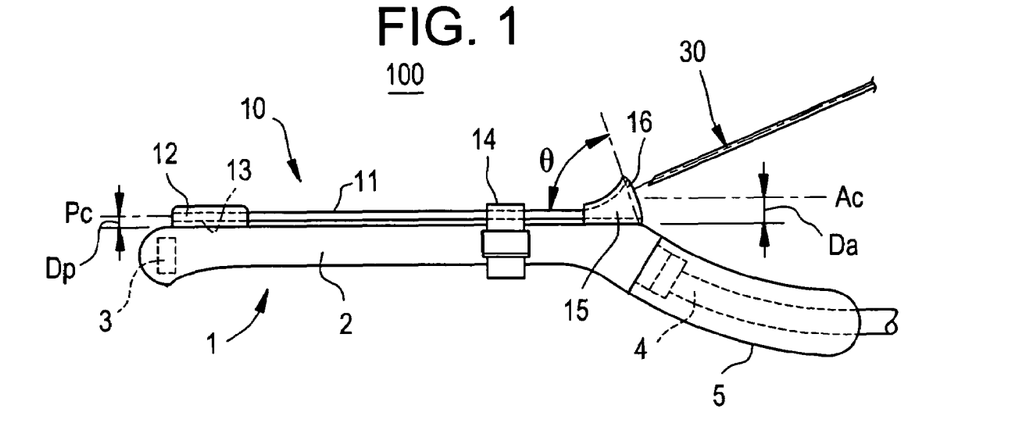
FIG. 1 is a right side view showing an ultrasonic biopsy probe of Example 1.
Figure 2:
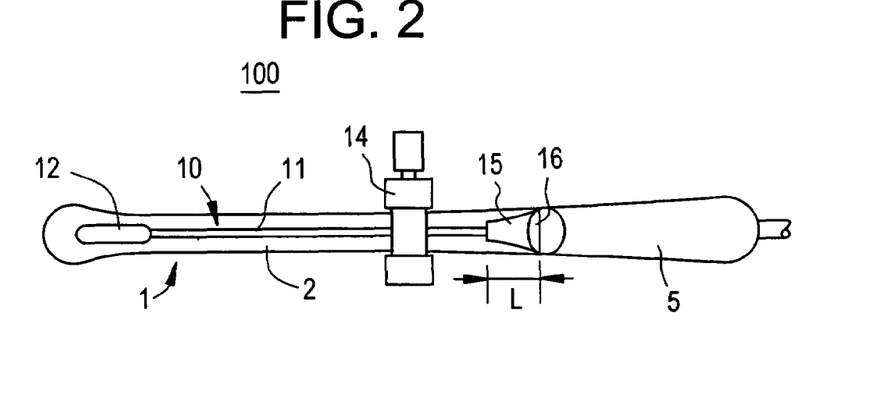
FIG. 2 is a plan view showing the ultrasonic biopsy probe of Example 1.
Figure 3:
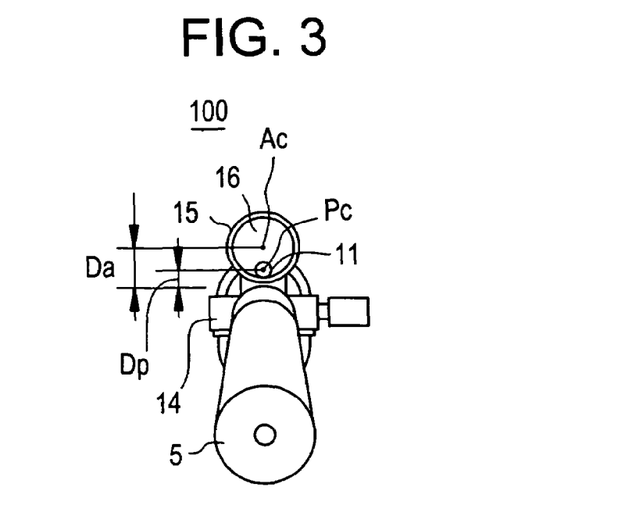
FIG. 3 is a rear view showing the ultrasonic biopsy probe of Example 1.

FIG. 1 a side view of an ultrasonic biopsy probe 100 of Example 1. FIG. 2 is a plan view of the ultrasonic biopsy probe 100. FIG. 3 is a rear view of the ultrasonic biopsy probe 100.

The ultrasonic biopsy probe 100 comprises an ultrasonic probe body 1, a needle guide 10 united with the ultrasonic probe body 1, and a needle 30.

The ultrasonic probe body 1 comprises an elongated trunk 2, ultrasonic transducers 3 contained in a spherical end at a first end of the elongated trunk 2, a cable 4 led out from a second end of the elongated trunk 2, and a grip 5 used by an operator to hold the ultrasonic probe body 1.

The needle guide 10 comprises a straight conduit 11 having a linear passage of an inner diameter that allows passage of the needle 30 (e.g., 2 mm), a head 12 of an elongated circular shape for rounding the first end and vicinity of the straight conduit 11, a hook 13 protruding from the bottom of the head 11 to be caught by the ultrasonic probe body 1, a fastener 14 for removably uniting the straight conduit 11 with the ultrasonic probe body 1, and a funnel 15 for increasing the diameter of an opening of the straight conduit 11 at the second end.

The straight conduit 11, head 12, hook 13, fastener 14 and funnel 15 are made of stainless steel, and assembled by silver-alloy brazing.

The length L of the funnel 15 is 8 mm or more.

The needle guide 10 may be alternatively made of a plastic so as to be disposable.

When the needle guide 10 is united with the ultrasonic probe body 1, the straight conduit 11 is in parallel to the center axis of the elongated trunk 2.

An opening 16 of the funnel 15 has a circular profile, and the opening face is curved. The opening face lies obliquely away from the grip 5 with respect to the center axis of the elongated trunk 2 (e.g., the angle of obliqueness ☐=45°-85°).

Moreover, a distance Da from a center Ac of the opening 16 of the funnel 15 to the ultrasonic probe body 1 (e.g., 20 mm) is larger than a distance Dp from a center Pc of an opening of the straight conduit 11 at the first end to the ultrasonic probe body 1 (e.g., 5 mm).

Figure 4:
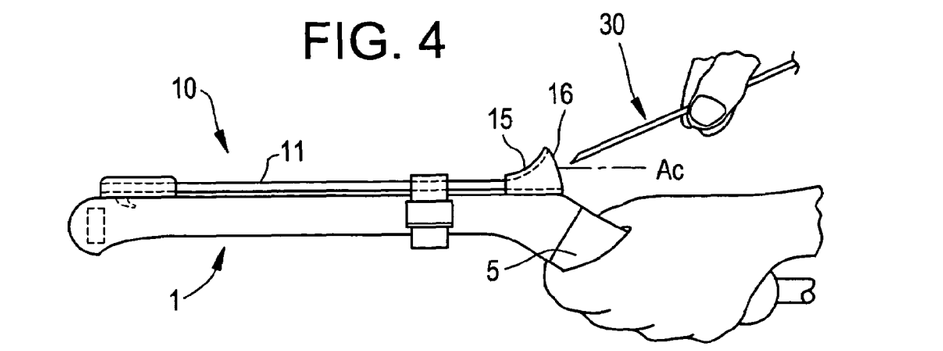
FIG. 4 is an explanatory view showing a condition immediately before inserting a needle into the ultrasonic biopsy probe of Example 1.

The operator holds the grip 5 as shown in FIG. 4, inserts a portion in which the ultrasonic transducers 3 are disposed into a medical patient, and conducts ultrasound transmission and reception.

When conducting needle prick, as shown in FIG. 4, the operator positions the needle tip of the needle 30 near the center Ac of the opening 16 in front of the opening 16 of the funnel 15.

At that time, since the distance Da from the center Ac of the opening 16 to the ultrasonic probe body 1 is larger than in the conventional case (Dp), the distance between the needle tip of the needle 30 and the hand of the operator is larger than in the conventional case, thus preventing the needle tip of the needle 30 from being touched by the hand of the operator.

Figure 5:
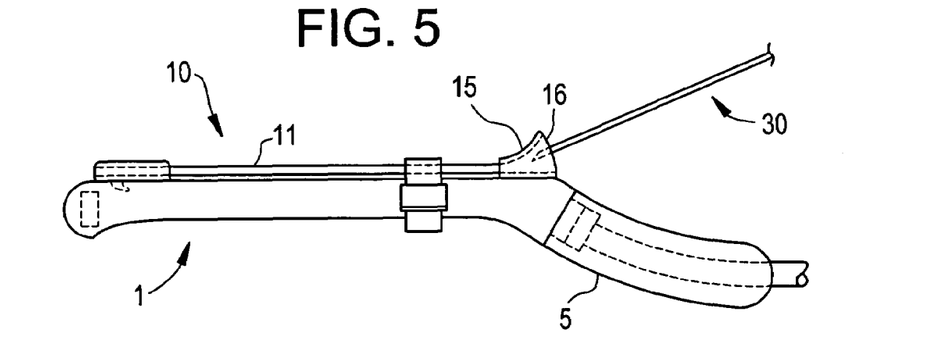
FIG. 5 is an explanatory view showing a condition immediately after inserting the needle into the ultrasonic biopsy probe of Example 1.

As shown in FIG. 5, the operator next moves the needle 30 toward the opening 16 to insert the needle tip of the needle 30 into the opening 16.

At that time, the operator is psychologically disposed to try to insert the needle tip as perpendicularly to the opening face as possible; and since the opening face of the opening 16 is oblique, the operator resultingly makes the needle 30 oblique so that the needle tip of the needle 30 comes closest to the hand of the operator. Therefore, if the operator focuses his/her attention merely to the needle tip of the needle 30 so that the needle tip of the needle 30 is not touched by his/her hand, no portion of the needle 30 will be touched by the hand of the operator holding the ultrasonic probe body.

Figure 6:
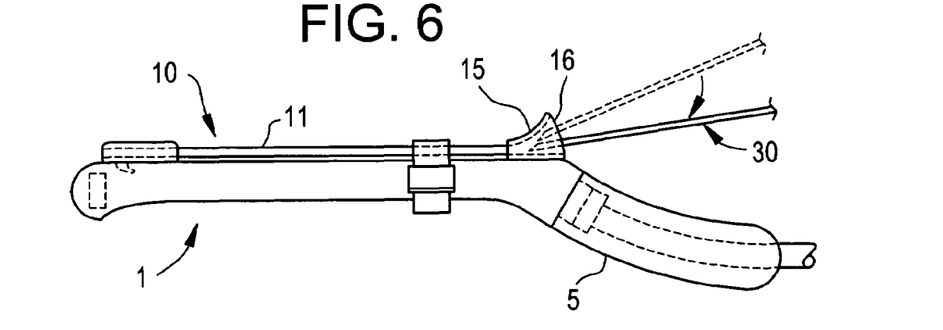
FIG. 6 is an explanatory view showing a process of inserting the needle into the ultrasonic biopsy probe of Example 1.

Next, as shown in FIG. 6, the operator moves the needle 30 while changing the attitude of the needle 30 so that the needle 30 is aligned with the center axis of the straight conduit 11.

At that time, since the needle tip of the needle 30 has been inserted into the funnel 15, the needle tip of the needle 30 is not touched by the hand of the operator.

Figure 7:
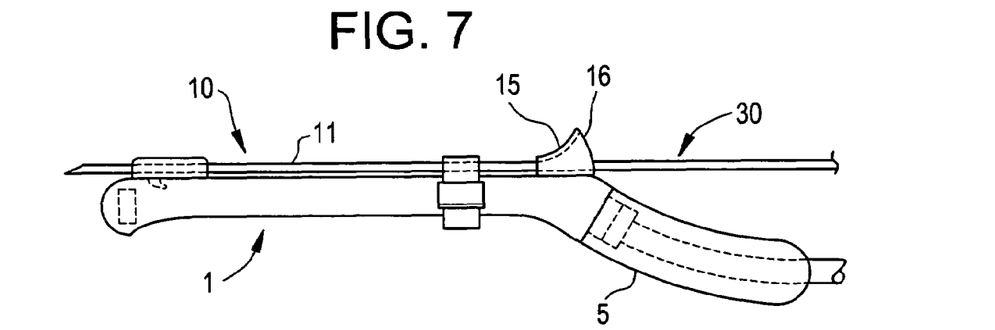
FIG. 7 is an explanatory view showing needle prick by the ultrasonic biopsy probe of Example 1.

Finally, as shown in FIG. 7, the operator inserts the needle 30 into the passage of the straight conduit 11, and pushes the needle tip out of the first opening of the straight conduit 11 to conduct a needle prick.

At that time, the direction of the needle 30 is guided by the passage of the straight conduit 11.

According to the ultrasonic biopsy probe 100 and needle guide 10 of Example 1, the needle 30 is prevented from being touched by the hand of the operator, thereby facilitating the needle-prick operation. Moreover, since the needle tip can be inserted into the opening 16 while obliquely holding the needle 30, it is easier to control the needle tip than in an operation of inserting the needle tip into the opening 16 while horizontally holding the needle 30.

EXAMPLE 2

Figure 8:
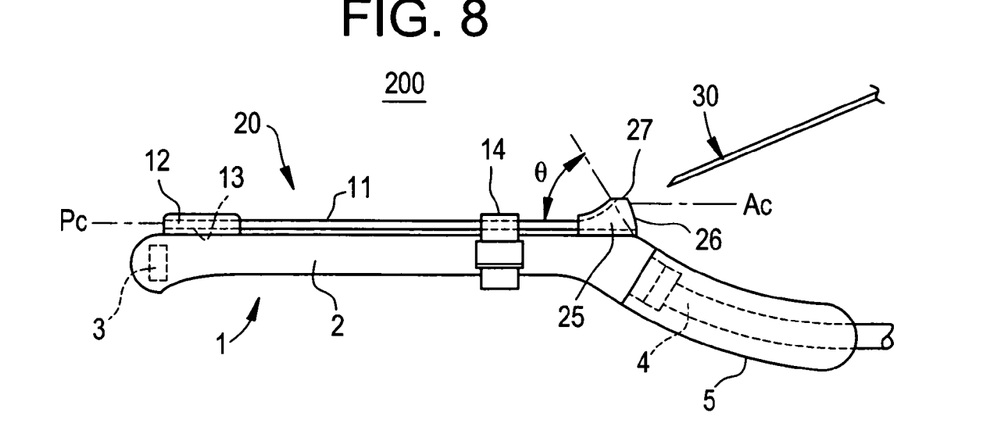
FIG. 8 is a right side view showing an ultrasonic biopsy probe of Example 2.
Figure 9:
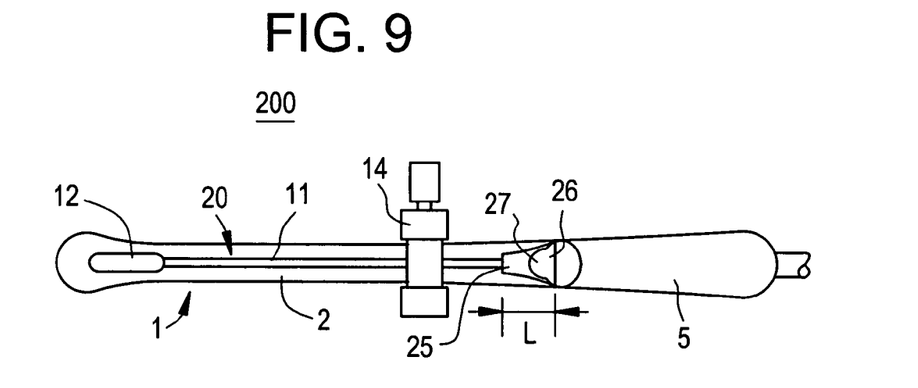
FIG. 9 is a plan view showing the ultrasonic biopsy probe of Example 2.
Figure 10:
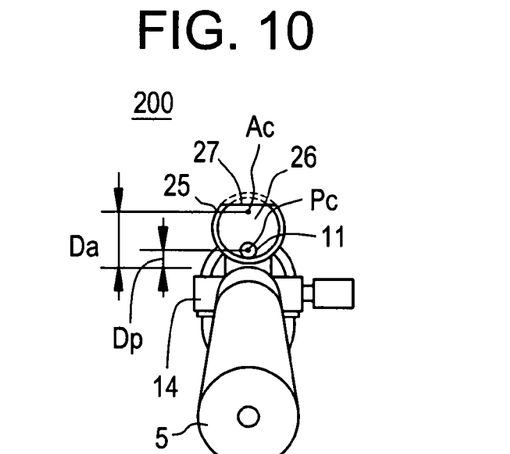
FIG. 10 is a rear view showing the ultrasonic biopsy probe of Example 2.

FIG. 8 is a side view of an ultrasonic biopsy probe 200 of Example 2. FIG. 9 is a plan view of the ultrasonic biopsy probe 200. FIG. 10 is a rear view of the ultrasonic biopsy probe 200.

The ultrasonic biopsy probe 200 comprises an ultrasonic probe body 1, a needle guide 20 united with the ultrasonic probe body 1, and a needle 30.

The ultrasonic probe body 1 comprises an elongated trunk 2, ultrasonic transducers 3 contained in a spherical end at a first end of the elongated trunk 2, a cable 4 led out from a second end of the elongated trunk 2, and a grip 5 used by the operator to hold the ultrasonic probe body 1.

The needle guide 20 comprises a straight conduit 11 having a linear passage of an inner diameter that allows passage of the needle 30 (e.g., 2 mm), a head 12 of an elongated circular shape for rounding the first end and vicinity of the straight conduit 111, a hook 13 protruding from the bottom of the head 11 to be caught by the ultrasonic probe body 1, a fastener 14 for removably uniting the straight conduit 11 with the ultrasonic probe body 1, and a funnel 25 for increasing the diameter of an opening of the straight conduit 11 at the second end.

The straight conduit 11, head 12, hook 13, fastener 14 and funnel 25 are made of stainless steel, and assembled by silver-alloy brazing.

The length L of the funnel 25 is 8 mm or more.

The needle guide 20 may be alternatively made of a plastic so as to be disposable.

When the needle guide 20 is united with the ultrasonic probe body 1, the straight conduit 11 is in parallel to the center axis of the elongated trunk 2.

An opening of the funnel 25 is comprised of a front opening 26 and an upper opening 27 connected to each other to have a profile like two circles connected to each other; the face of the front opening 26 is curved, the face of the upper opening 27 is planar, and the opening face is bent as a whole. The face of the front opening 26 lies obliquely away from the grip 5 with respect to the center axis of the elongated trunk 2 (e.g., the angle of obliqueness ☐=45°-85°). The face of the upper opening 27 is in parallel with the center axis of the elongated trunk 2. The opening face as a whole lies obliquely away from the grip 5 with respect to the center axis of the elongated trunk 2 (e.g., the angle of obliqueness ☐=45°-85°).

Moreover, a distance Da from a center Ac of the opening as a whole of the funnel 15 to the ultrasonic probe body 1 (e.g., 20 mm) is larger than a distance Dp from a center Pc of an opening of the straight conduit 11 at the first end to the ultrasonic probe body 1 (e.g., 5 mm).

Figure 11:
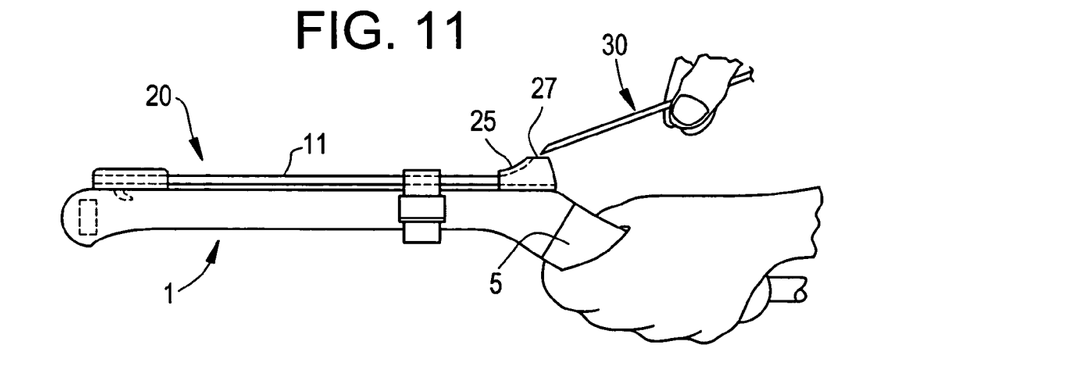
FIG. 11 is an explanatory view showing a condition immediately before inserting a needle into the ultrasonic biopsy probe of Example 2.

The operator holds the grip 5 as shown in FIG. 11, inserts a portion in which the ultrasonic transducers 3 are disposed into a medical patient, and conducts ultrasound transmission and reception.

When conducting a needle prick, as shown in FIG. 11, the operator positions the needle tip of the needle 30 just above the upper opening 27 of the funnel 25.

At that time, since the upper opening 27 is substantially away from the hand of the operator, the needle tip of the needle 30 is not touched by the hand of the operator.

Figure 12:
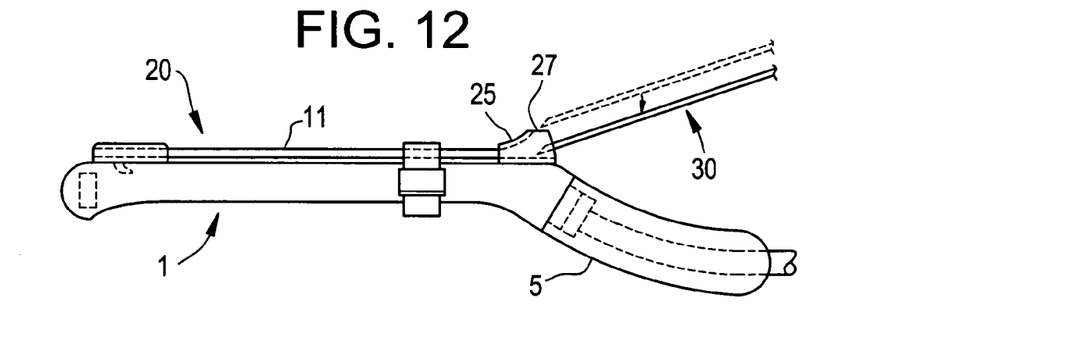
FIG. 12 is an explanatory view showing a condition immediately after inserting the needle into the ultrasonic biopsy probe of Example 2.

As shown in FIG. 12, the operator next moves the needle 30 down to the upper opening 27 to insert the needle tip of the needle 30 through the upper opening 27 into the funnel 25.

Figure 13:
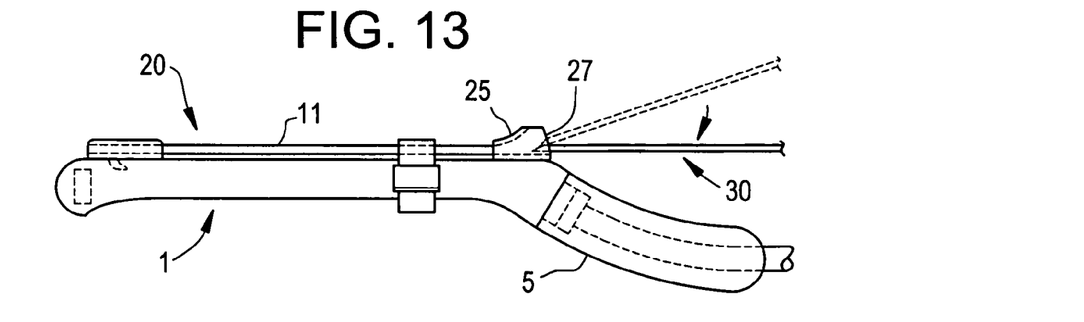
FIG. 13 is an explanatory view showing a process of inserting the needle into the ultrasonic biopsy probe of Example 2.

Next, as shown in FIG. 13, the operator moves the needle 30 while changing the attitude of the needle 30 so that the needle 30 is aligned with the center axis of the straight conduit 11.

At that time, since the needle tip of the needle 30 has been inserted into the funnel 25, the needle tip of the needle 30 is not touched by the hand of the operator.

Figure 14:
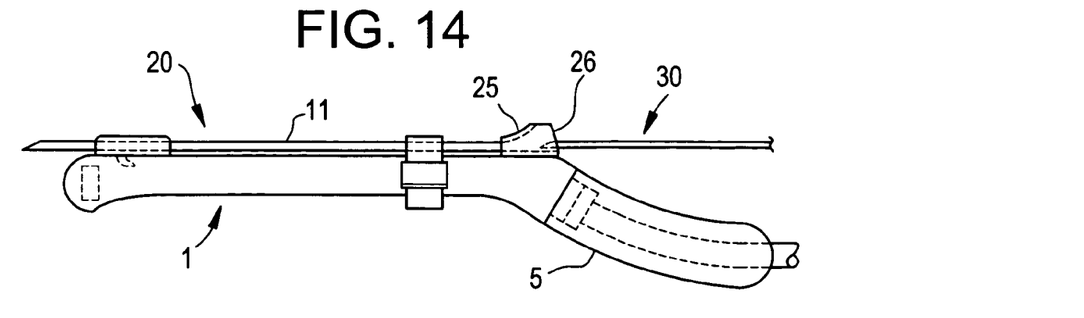
FIG. 14 is an explanatory view showing needle prick by the ultrasonic biopsy probe of Example 2.

Finally, as shown in FIG. 14, the operator inserts the needle 30 into the passage of the straight conduit 11, and pushes the needle tip out of the first opening of the straight conduit 11 to conduct needle prick.

At that time, the direction of the needle 30 is guided by the passage of the straight conduit 11.

According to the ultrasonic biopsy probe 200 and needle guide 20 of Example 2, the needle 30 is prevented from being touched by the hand of the operator, thereby facilitating the needle-prick operation.

EXAMPLE 3

Figure 15:
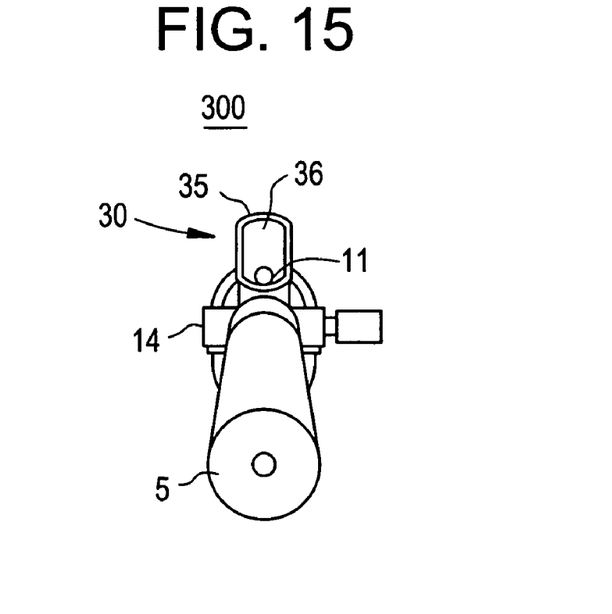
FIG. 15 is a rear view showing an ultrasonic biopsy probe of Example 3.

An ultrasonic biopsy probe 300 shown in FIG. 15 employs a needle guide 30 instead of the needle guide 10 in the ultrasonic biopsy probe 100 of Example 1.

The needle guide 30 employs a funnel 35 having an opening 36 of an elongated circular profile, instead of the funnel 15 in the needle guide 10 of Example 1.

According to the ultrasonic biopsy probe 300 and needle guide 30 of Example 3, the needle 30 is prevented from being touched by the hand of the operator, thereby facilitating the needle-prick operation.

EXAMPLE 4

Figure 16:
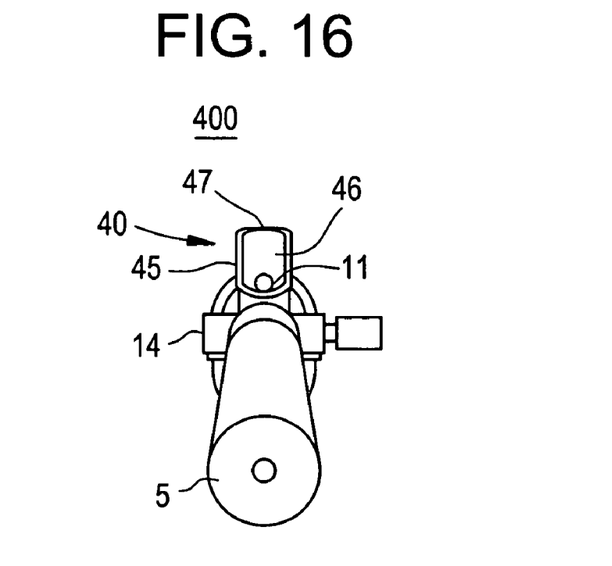
FIG. 16 is a rear view showing an ultrasonic biopsy probe of Example 4.

An ultrasonic biopsy probe 400 shown in FIG. 16 employs a needle guide 40 instead of the needle guide 30 in the ultrasonic biopsy probe 300 of Example 3.

The needle guide 40 employs a funnel 45 having an opening in which a front opening 46 and an upper opening 47 are connected to each other, instead of the funnel 35 in the needle guide 30 of Example 3.

According to the ultrasonic biopsy probe 400 and needle guide 40 of Example 4, the needle 30 is prevented from being touched by the hand of the operator, thereby facilitating the needle-prick operation.

EXAMPLE 5

Figure 17:
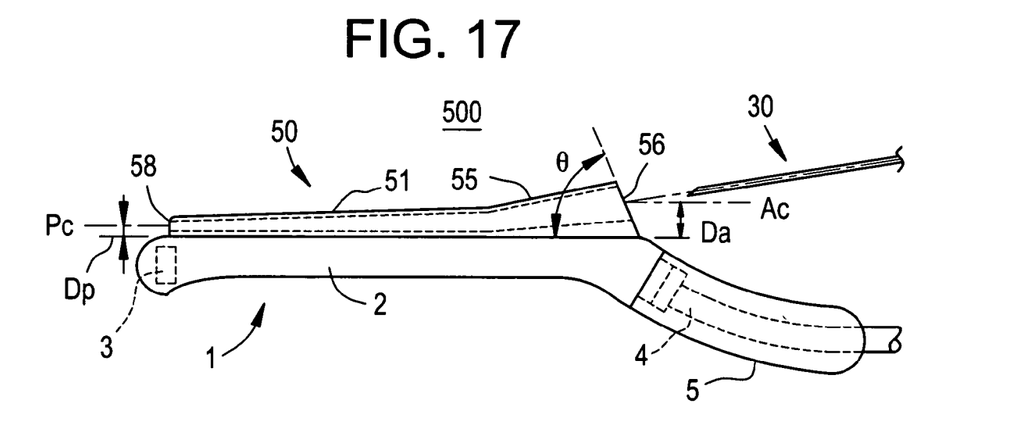
FIG. 17 is a right side view showing an ultrasonic biopsy probe of Example 5.

An ultrasonic biopsy probe 500 shown in FIG. 17 employs a needle guide 50 instead of the needle guide 10 in the ultrasonic biopsy probe 100 of Example 1.

The needle guide 50 is comprised of a flared tube 51 having a passage gradually outspreading from a first opening 58 of an inner diameter that allows passage of the needle 30 (e.g., 2 mm) to a second opening 56 larger than the first opening 58, and is united with the ultrasonic probe body 1 by being fitted into the ultrasonic probe body 1.

The flared tube 51 has a less outspread portion that is to be inserted into the medical patient, and a more outspread portion that is not to be inserted into the medical patient.

The flared tube 51 is made of stainless steel.

The needle guide 50 may be made of a plastic so as to be disposable.

The second opening 56 has a circular profile, and its opening face is planar. The opening face lies obliquely away from the grip 5 with respect to the center axis of the elongated trunk 2 (e.g., the angle of obliqueness □=45°-85°).

Moreover, a distance Da from a center Ac of the second opening 56 to the ultrasonic probe body 1 (e.g., 20 mm) is larger than a distance Dp from a center Pc of the first opening of the flared tube 51 to the ultrasonic probe body 1 (e.g., 5 mm).

Figure 18:
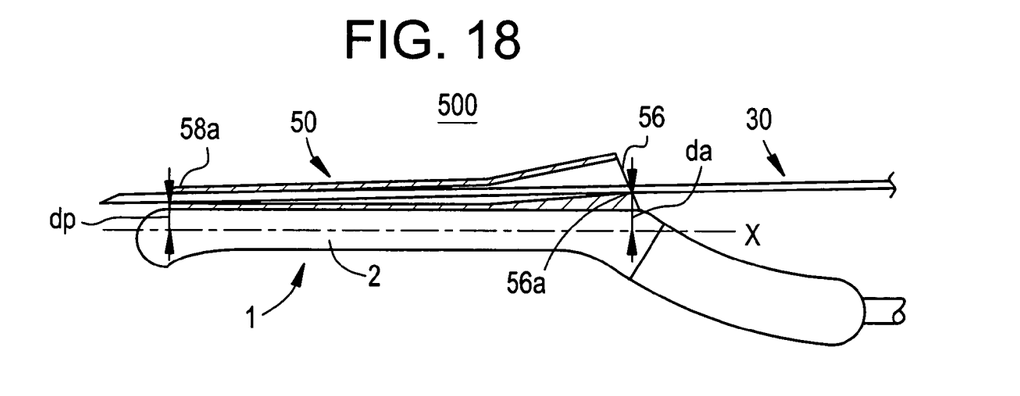
FIG. 18 is a partial cross-sectional view of the ultrasonic biopsy probe of Example 5.

As shown in FIG. 18, a distance da from a second opening bottom portion 56a to the center axis X of the elongated trunk 2 is larger than a distance dp from the lowest portion of the needle 30 to the center axis X of the elongated trunk 2 when the needle 30 is abutted against a first opening top portion 58a.

Thus, the needle 30 is inserted obliquely with respect to the center axis X of the elongated trunk 2.

According to the ultrasonic biopsy probe 500 and needle guide 50 of Example 5, the needle 30 is prevented from being touched by the hand of the operator, thereby facilitating the needle-prick operation. Moreover, since the pricking operation with the needle 30 can be achieved while obliquely holding the needle 30, it is easier to control the needle 30 than in an operation with the horizontally held needle 30.

EXAMPLE 6

Figure 19:
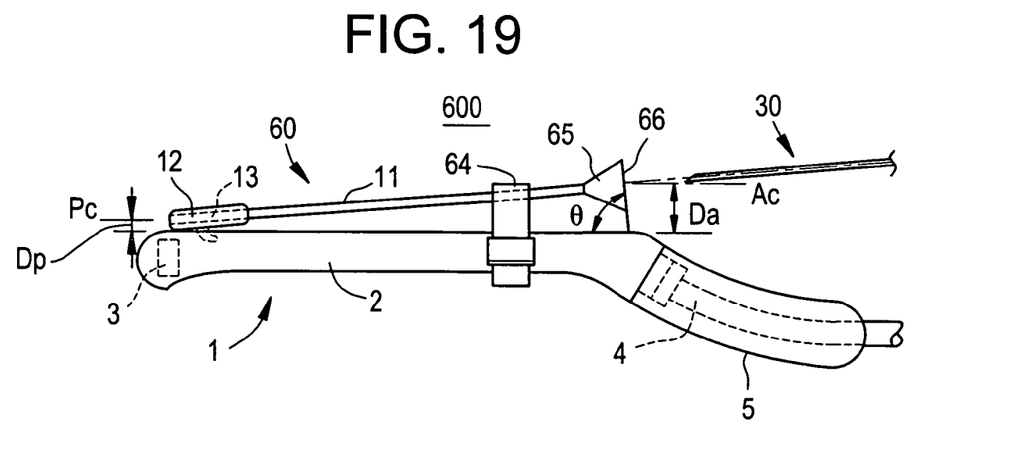
FIG. 19 is a right side view showing an ultrasonic biopsy probe of Example 6.

An ultrasonic biopsy probe 600 shown in FIG. 19 employs a needle guide 60 instead of the needle guide 10 in the ultrasonic biopsy probe 100 of Example 1.

The needle guide 60 comprises a straight conduit 11 having a linear passage of an inner diameter that allows passage of the needle 30 (e.g., 2 mm), a head 12 of an elongated circular shape for rounding the first end and vicinity of the straight conduit 11, a hook 13 protruding from the bottom of the head 11 to be caught by the ultrasonic probe body 1, a fastener 64 for removably uniting the straight conduit 11 with the ultrasonic probe body 1, and a funnel 65 for increasing the diameter of an opening of the straight conduit 11 at the second end.

The straight conduit 11, head 12, hook 13, fastener 64 and funnel 65 are made of stainless steel, and assembled by silver-alloy brazing.

The length L of the funnel 65 is 8 mm or more.

The needle guide 60 may be alternatively made of a plastic so as to be disposable.

When the needle guide 60 is united with the ultrasonic probe body 1, the straight conduit 11 is oblique with respect to the center axis of the elongated trunk 2.

An opening 66 of the funnel 65 has a circular profile, and its opening face is planar. The opening face lies obliquely away from the grip 5 with respect to the center axis of the elongated trunk 2 (e.g., the angle of obliqueness □=45°-85°).

Moreover, a distance Da from a center Ac of the opening 66 of the funnel 65 to the ultrasonic probe body 1 (e.g., 20 mm) is larger than a distance Dp from a center Pc of an opening of the straight conduit 11 at the first end to the ultrasonic probe body 1 (e.g., 5 mm).

According to the ultrasonic biopsy probe 600 and needle guide 60 of Example 6, the needle 30 is prevented from being touched by the hand of the operator, thereby facilitating the needle-prick operation. Moreover, since the operation of pricking with the needle 30 can be achieved while obliquely holding the needle 30, it is easier to control the needle 30 than in an operation with the horizontally held needle 30.

Many widely different embodiments of the invention may be configured without departing from the spirit and the scope of the present invention. It should be understood that the present invention is not limited to the specific embodiments described in the specification, except as defined in the appended claims.

The invention claimed is:

1. A needle guide removably united with an ultrasonic probe body, said ultrasonic probe body having an elongated trunk provided with ultrasonic transducers at a first end of said elongated trunk and a cable led out from a second end of said elongated trunk for conducting ultrasound transmission and reception with said first end inserted into a subject, said needle guide comprising a conduit having a first opening and an opposing second opening larger than said first opening, wherein when said needle guide is united with said ultrasonic probe body so that said first opening lies near said first end and said second opening lies near said second end, and a distance between a center of said second opening and said ultrasonic probe body is larger than a distance between a center of said first opening and said ultrasonic probe body, said second opening configured to facilitate inserting a needle into said needle guide at an oblique angle with respect to said elongated trunk.

2. The needle guide of claim 1, wherein the opening face of said second opening is oblique with respect to the center axis of said elongated trunk when said needle guide is united with said ultrasonic probe body.

3. The needle guide of claim 1, wherein an opening face of said second opening is a bent face created by connecting two planes at different angles with respect to the center axis of said elongated trunk when said needle guide is united with said ultrasonic body.

4. The needle guide of claim 1, wherein said needle guide comprises a straight conduit portion having a linear passage of an inner diameter that allows passage of a needle, and a funnel portion formed by increasing the diameter of an opening of said straight conduit portion at one end, said needle guide is united with said ultrasonic probe body so that said straight conduit portion lies near said first end and said funnel portion lies near said second end, a center of an opening of said funnel portion is offset from the center axis of said straight conduit portion so that a distance between the center of the opening of said funnel portion and said ultrasonic probe body is larger than a distance between a center of an opening of said straight conduit portion at the other end and said ultrasonic probe body.

5. The needle guide of claim 4, wherein an opening face of said funnel portion is oblique with respect to the center axis of said straight conduit portion.

6. The needle guide of claim 4, wherein the opening face of said funnel portion is a bent face created by connecting two planes at different angles with respect to the center axis of said straight conduit portion.

7. The needle guide of claim 1, wherein said needle guide comprises a flared tube having a passage outspreading from a first opening to a second opening larger than said first opening, said needle guide is united with said ultrasonic probe body so that said first opening lies near said first end and said second opening lies near said second end, and a distance between a center of said second opening and said ultrasonic probe body is larger than a distance between a center of said first opening and said ultrasonic probe body.

8. The needle guide of claim 7, wherein when a needle is abutted against a first opening top portion and a second opening bottom portion, said needle is oblique with respect to the center axis of said elongated trunk.

9. The needle guide of claim 1, wherein said needle guide comprises a straight conduit portion having a linear passage of an inner diameter that allows passage of a needle, a funnel portion formed by increasing the diameter of an opening of said straight conduit portion at one end, and a fastener for uniting said needle guide with said ultrasonic probe body so that said straight conduit portion lies near said first end and said funnel portion lies near said second end, when said needle guide is united with said ultrasonic body, said fastener achieves the uniting while making the center axis of said straight conduit portion oblique with respect to the center axis of said elongated trunk so that a distance between a center of the opening of said funnel portion and said ultrasonic probe body is larger than a distance between a center of the opening of said straight conduit portion at the other end and said ultrasonic probe body.

10. An ultrasonic biopsy probe comprising an ultrasonic probe body and a needle guide united with said ultrasonic probe body, said ultrasonic probe body having an elongated trunk provided with ultrasonic transducers at a first end of said elongated trunk and a cable led out from a second end of said elongated trunk for conducting ultrasound transmission and reception with said first end inserted into a subject, wherein said needle guide comprises a conduit having a first opening and an opposing second opening larger than said first opening, when said needle guide is united with said ultrasonic probe body so that said first opening lies near said first end and said second opening lies near said second end, and a distance between a center of said second opening and said ultrasonic probe body is larger than a distance between a center of said first opening and said ultrasonic probe body, said second opening configured to facilitate inserting a needle into said needle guide at an oblique angle with respect to said elongated trunk.

11. The ultrasonic biopsy probe of claim 10, wherein an opening face of said second opening is oblique with respect to the center axis of said elongated trunk when said needle guide is united with said ultrasonic probe body.

12. The ultrasonic biopsy probe of claim 10, wherein the opening face of said second opening is a bent face created by connecting two planes at different angles with respect to the center axis of said elongated trunk when said needle guide is united with said ultrasonic body.

13. The ultrasonic biopsy probe of claim 10, wherein said needle guide comprises a straight conduit portion having a linear passage of an inner diameter that allows passage of the needle, and a funnel portion formed by increasing the diameter of an opening of said straight conduit portion at one end, said needle guide is united with said ultrasonic probe body so that said straight conduit portion lies near said first end and said funnel portion lies near said second end, a center of an opening of said funnel portion is offset from the center axis of said straight conduit portion so that a distance between the center of the opening of said funnel portion and said ultrasonic probe body is larger than a distance between a center of an opening of said straight conduit portion at the other end and said ultrasonic probe body.

14. The ultrasonic biopsy probe of claim 13, wherein an opening face of said funnel portion is oblique with respect to the center axis of said straight conduit portion.

15. The ultrasonic biopsy probe of claim 13, wherein the opening face of said funnel portion is a bent face created by connecting two planes at different angles with respect to the center axis of said straight conduit portion.

16. The ultrasonic biopsy probe of claim 10, wherein said needle guide comprises a flared tube having a passage outspreading from a first opening to a second opening larger than said first opening, said needle guide is united with said ultrasonic probe body so that said first opening lies near said first end and said second opening lies near said second end, and a distance between a center of said second opening and said ultrasonic probe body is larger than a distance between a center of said first opening and said ultrasonic probe body.

17. The ultrasonic biopsy probe of claim 16, wherein when a needle is abutted against a first opening top portion and a second opening bottom portion, said needle is oblique with respect to the center axis of said elongated trunk.

18. The ultrasonic biopsy probe of claim 10, wherein said needle guide comprises a straight conduit portion having a linear passage of an inner diameter that allows passage of a needle, a funnel portion formed by increasing the diameter of an opening of said straight conduit portion at one end, and a fastener for uniting said needle guide with said ultrasonic probe body so that said straight conduit portion lies near said first end and said funnel portion lies near said second end, wherein when said needle guide is united with said ultrasonic body, said fastener achieves the uniting while making the center axis of said straight conduit portion oblique with respect to the center axis of said elongated trunk so that a distance between a center of the opening of said funnel portion and said ultrasonic probe body is larger than a distance between a center of the opening of said straight conduit portion at the other end and said ultrasonic probe body.

* * * * *